(12) United States Patent
Vezzu et al.

(10) Patent No.: US 10,973,682 B2
(45) Date of Patent: Apr. 13, 2021

(54) SURGICAL INSTRUMENT WITH ADHESION OPTIMIZED EDGE CONDITION

(71) Applicant: Alcon Inc., Fribourg (CH)

(72) Inventors: Guido Vezzu, Pfungen (CH); Reto Grueebler, Greifensee (CH)

(73) Assignee: Alcon Inc., Fribourg (CH)

( * ) Notice: Subject to any disclaimer, the term of this patent is extended or adjusted under 35 U.S.C. 154(b) by 287 days.

(21) Appl. No.: 14/550,470

(22) Filed: Nov. 21, 2014

(65) Prior Publication Data

US 2015/0238355 A1 Aug. 27, 2015

Related U.S. Application Data

(60) Provisional application No. 61/943,805, filed on Feb. 24, 2014.

(51) Int. Cl.
| | |
|---|---|
| *A61F 9/007* | (2006.01) |
| *A61B 17/30* | (2006.01) |
| *A61B 17/29* | (2006.01) |
| *A61B 17/00* | (2006.01) |

(52) U.S. Cl.
CPC ............ *A61F 9/007* (2013.01); *A61B 17/29* (2013.01); *A61B 17/30* (2013.01); *A61F 9/00736* (2013.01); *A61B 2017/00858* (2013.01); *A61B 2017/00951* (2013.01); *A61B 2017/2945* (2013.01); *A61B 2017/305* (2013.01)

(58) Field of Classification Search
CPC ......... A61B 17/30; A61B 2017/00858; A61B 2017/00951; A61B 2017/305; A61B 17/29; A61B 17/28; A61F 9/007; A61F 9/00763; G04D 1/02; G04D 1/021; B25B 7/00; B25B 27/205; A61C 3/14; A45D 26/0066

USPC ............................................ 606/207
See application file for complete search history.

(56) References Cited

U.S. PATENT DOCUMENTS

| | | |
|---|---|---|
| 2,795,225 A | 6/1957 | Sovatkin et al. |
| 4,671,283 A | 6/1987 | Hoskin et al. |
| 4,693,246 A | 9/1987 | Reimels |
| 4,994,079 A | 2/1991 | Genese et al. |
| 5,078,716 A | 1/1992 | Doll |

(Continued)

FOREIGN PATENT DOCUMENTS

| | | |
|---|---|---|
| CA | 2825008 A1 | 7/2012 |
| CN | 101637419 A | 2/2010 |

(Continued)

OTHER PUBLICATIONS

Valentin-Rodriguez, et al, "Quantitative Analysis of Human Internal Limiting Membrane Extracted from Patients with Macular Holes", Langmuir, Jun. 2010, 26(15), pp. 12810-12816 (DOI: 10.102/la101797e).

(Continued)

*Primary Examiner* — George J Ulsh

(57) ABSTRACT

A surgical instrument such as for use in vitreoretinal surgeries is described. The surgical instrument may include a pair of pincers resiliently biased toward an opened configuration and being movable toward each other into a closed configuration to engage a membrane. Each pincer may include a rounded grasping edge. The grasping edges may include a textured surface operable to induce a capillary effect between a membrane and the forceps to promote adhesion therebetween.

18 Claims, 6 Drawing Sheets

(56) References Cited

U.S. PATENT DOCUMENTS

| | | |
|---|---|---|
| 5,208,111 A | 5/1993 | Decher et al. |
| 5,222,973 A | 6/1993 | Sharpe et al. |
| 5,234,458 A | 8/1993 | Metais |
| 5,340,354 A | 8/1994 | Anderson et al. |
| 5,425,596 A | 6/1995 | Steere et al. |
| 5,496,330 A | 3/1996 | Bates et al. |
| 5,601,572 A | 2/1997 | Middleman et al. |
| 5,634,918 A | 6/1997 | Richards |
| 5,700,559 A | 12/1997 | Sheu et al. |
| 5,739,237 A | 4/1998 | Russell et al. |
| 5,792,145 A | 8/1998 | Bates et al. |
| 5,810,881 A | 9/1998 | Hoskin et al. |
| 5,855,586 A | 1/1999 | Habara et al. |
| 5,919,202 A | 7/1999 | Yoon |
| 5,921,998 A | 7/1999 | Tamo et al. |
| 5,972,021 A | 10/1999 | Huttner et al. |
| 6,077,274 A | 6/2000 | Ouchi et al. |
| 6,120,518 A | 9/2000 | Mark et al. |
| 6,267,759 B1 | 7/2001 | Quick |
| 6,340,354 B1 | 1/2002 | Rambin |
| D456,077 S | 4/2002 | Etter et al. |
| 6,451,037 B1 | 9/2002 | Chandrasekaran et al. |
| 6,464,629 B1 | 10/2002 | Boone et al. |
| 6,488,695 B1 | 12/2002 | Hickingbotham |
| 6,575,989 B1 | 6/2003 | Scheller et al. |
| 6,592,600 B1 | 7/2003 | Nicolo |
| 6,685,725 B2 | 2/2004 | Attinger et al. |
| 6,730,076 B2 | 5/2004 | Hickingbotham |
| 6,772,765 B2 | 8/2004 | Scheller et al. |
| 6,920,965 B2 | 7/2005 | Burgdorf et al. |
| 6,995,336 B2 | 2/2006 | Hunt et al. |
| 7,251,893 B2 | 8/2007 | Cohen et al. |
| 7,335,271 B2 | 2/2008 | Autumn |
| 7,410,606 B2 | 8/2008 | Appleby et al. |
| 7,582,327 B2 | 9/2009 | Qiu et al. |
| 7,867,230 B2 | 1/2011 | Asahara et al. |
| 7,893,413 B1 | 2/2011 | Appleby et al. |
| 8,150,506 B2 | 4/2012 | Kaushal et al. |
| 8,241,321 B2 | 8/2012 | Scheller et al. |
| 8,425,596 B2 | 4/2013 | Britton et al. |
| 8,469,993 B2 | 6/2013 | Rothberg et al. |
| 8,579,887 B2 | 11/2013 | Hanlon et al. |
| 8,795,196 B2 | 8/2014 | Cho et al. |
| 8,821,444 B2 | 9/2014 | Scheller et al. |
| 9,060,842 B2 | 6/2015 | Karp et al. |
| 9,138,346 B2 | 9/2015 | Scheller et al. |
| 9,173,772 B1 | 11/2015 | Scheller et al. |
| 9,174,184 B2 | 11/2015 | Kang et al. |
| 9,204,995 B2 | 12/2015 | Scheller et al. |
| 9,226,762 B2 | 1/2016 | Scheller et al. |
| 9,247,951 B1 | 2/2016 | Scheller et al. |
| 9,320,534 B2 | 4/2016 | Vezzu |
| 9,428,254 B1 | 8/2016 | Scheller et al. |
| 9,586,044 B2 | 3/2017 | Ross |
| 9,592,074 B2 | 3/2017 | Hanlon et al. |
| 9,629,645 B2 | 4/2017 | Scheller et al. |
| 9,775,943 B2 | 4/2017 | Scheller et al. |
| 9,795,506 B2 | 10/2017 | Scheller et al. |
| 2002/0068954 A1 | 6/2002 | Foster |
| 2003/0060812 A1 | 3/2003 | Hickingbotham |
| 2004/0020015 A1 | 2/2004 | Yokemura et al. |
| 2004/0193214 A1 | 9/2004 | Scheller |
| 2004/0260337 A1 | 12/2004 | Freed |
| 2007/0043352 A1* | 2/2007 | Garrison ............ A61B 18/1445 606/51 |
| 2007/0179512 A1 | 8/2007 | Olsen et al. |
| 2007/0225785 A1 | 9/2007 | Park et al. |
| 2007/0239202 A1 | 10/2007 | Rodriguez |
| 2007/0282348 A1 | 12/2007 | Lumpkin |
| 2008/0021399 A1 | 1/2008 | Spaide |
| 2008/0058761 A1 | 3/2008 | Spaide |
| 2008/0167576 A1 | 7/2008 | Cho et al. |
| 2008/0183199 A1 | 7/2008 | Attinger |
| 2009/0030448 A1 | 1/2009 | Andre |
| 2010/0226943 A1 | 9/2010 | Brennan et al. |
| 2011/0015669 A1* | 1/2011 | Corcosteugi ........... A61B 17/29 606/207 |
| 2011/0021965 A1 | 1/2011 | Karp et al. |
| 2011/0144567 A1 | 6/2011 | Sorensen et al. |
| 2011/0270221 A1 | 11/2011 | Ross |
| 2011/0282190 A1 | 11/2011 | Caffey et al. |
| 2013/0059113 A1 | 3/2013 | Hatton et al. |
| 2013/0204245 A1 | 8/2013 | Ivanisevic et al. |
| 2014/0135820 A1 | 5/2014 | Schaller et al. |
| 2014/0172010 A1 | 6/2014 | Vezzu |
| 2014/0277110 A1* | 9/2014 | Scheller ................ A61B 17/30 606/207 |
| 2014/0379024 A1 | 12/2014 | Schaller et al. |
| 2015/0088193 A1 | 3/2015 | Scheller et al. |
| 2015/0297278 A1 | 10/2015 | Scheller |
| 2016/0066940 A1 | 3/2016 | Scheller et al. |
| 2016/0074219 A1 | 3/2016 | Scheller et al. |
| 2017/0119419 A1 | 5/2017 | Scheller et al. |
| 2017/0296382 A1 | 10/2017 | Mukai |

FOREIGN PATENT DOCUMENTS

| | | |
|---|---|---|
| CN | 201624872 U | 11/2010 |
| CN | 102565057 A | 7/2012 |
| CN | 104837444 A | 8/2015 |
| CN | 104994793 A | 10/2015 |
| CN | 204839914 U | 12/2015 |
| DE | 102009033015 A1 | 1/2011 |
| EP | 1406536 A2 | 1/2003 |
| EP | 1295580 A1 | 3/2003 |
| EP | 1511433 A1 | 3/2005 |
| EP | 1463455 B1 | 8/2005 |
| EP | 1986581 B1 | 3/2012 |
| EP | 2214590 B1 | 8/2016 |
| GB | 2086792 A | 5/1982 |
| JP | S57110238 A | 7/1982 |
| JP | 2003159270 A | 6/2003 |
| JP | 2005529678 A | 10/2005 |
| JP | 2006527633 A | 12/2006 |
| RU | 43173 U1 | 1/2005 |
| SU | 117617 A1 | 11/1958 |
| WO | 1995011629 A1 | 5/1995 |
| WO | 9924091 A1 | 5/1999 |
| WO | 2003105705 A1 | 12/2003 |
| WO | 2004020015 A1 | 3/2004 |
| WO | 2005086772 A2 | 9/2005 |
| WO | 2007103671 A3 | 9/2007 |
| WO | 2008011225 A2 | 1/2008 |
| WO | 2009067649 A2 | 5/2009 |
| WO | 2011097578 A1 | 8/2011 |
| WO | 201197578 A2 | 11/2011 |
| WO | 2011143388 A2 | 11/2011 |
| WO | 2012064361 A1 | 5/2012 |
| WO | 2014078049 A1 | 5/2014 |
| WO | 2014092956 A1 | 6/2014 |
| WO | 2016063707 | 4/2016 |

OTHER PUBLICATIONS

Rabinovich, et al, "Adhesion between Nanoscale Rough Surfaces, I. Role of Asperity Geometry", J.Colloid & Interface Sci., Aug. 2000, 232, pp. 10-16 (DOI:10.1006/jcis.2000.7167).

Rabinovich, et al, "Adhesion between Nanoscale Rough Surfaces II. Measurement and Comparison with Theory", J.Colloid & Interface Sci., Aug. 2000, 232, pp. 17-24 (DOI:10.1006/jcis.2000.7168).

PCT/EP2015/052791; International Searching Authority, International Search Report, dated Apr. 24, 2015, 5 pgs.

Bhisitkul, R.B., Development of Microelectromechanical Systems (MEMS) Forceps for Intraocular Surgery, C.G. Keller, Br. J. Ophthalmol, 2005; 89: pp. 1586-1588.

"Grieshaber Revolution DSP", ALCON, Vitreoretical Product Catalog, 6 pgs., 2012 Novartis Jul. 2012.

Pavoor, P., Wear Reduction of Orthopaedic Bearing Surfaces Using Polyelectrolyte Multilayer Nanocoatings, Elsevier, 2006, pp. 1527-1533.

Prosecution History, U.S. Appl. No. 14/550,470, 42 pages, Jan. 6, 2015.

(56) References Cited

OTHER PUBLICATIONS

United States Patent and Trademark Office, U.S. Appl. No. 61/302,064, filed Feb. 5, 2010, pp. 1-41.
United States Patent and Trademark Office, U.S. Appl. No. 61/389,573, filed Oct. 4, 2010, pp. 1-37.
Valentin-Rodriguez, C., Quantitative Analysis of Human Internal Limiting Membrane Extracted from Patients with Macular Holes, Langmuir, 2010, 26(15), pp. 12810-12816.
Valentin-Rodriguez, C., Turning the Adhesion of Layer-by-Layer Films to the Physicochemical Properties of Inner Limiting Membranes Using Nanoparticles, Elsevier, 2011, pp. 616-624.
Alexander Vankov et al., Electro-adhesive Forceps for Tissue Manipulation, Department of Ophthalmology, School of Medicine, Stanford Univ.
Celimar Valentine-Rodriguez, et al., Turning the Adhesion of Layer-by-Layer Films to the Physiochemical Properties of Inner Limiting Membranes using Navo Particles.
Celimar Valentine-Rodriguez, et al., Quantitative Analysis of Human Internal Limiting Membrane Extraction from Patients with Maclar Holes, Jul. 2, 2010.
M. Hess et al., Terminology of Polymers Containing Ionizable or Ionic Groups and of Polymers Containing Ions 2006.
Celimar Valentine-Rodriguez, et al., Surface Modification of Vitreorectinal Surgical Instruments with Layer-by-Layer Films. 2011.
Nevdeck, Gerold W. et al., Fabrication of a Silicon Micro-Scalpel with a Nanometer Cutting Edge, May 1, 2003.
Development of Microelectromechanical Systems (MEMS) Forceps for Intraocular Surgery, R.B. Bhisitkul, CG Keller, Br. J Ophthalmol 2005; 89:1586-1588.
Nlikkhah M, et al. (2012). Engineering microsale topographies to control the cell-substrate interface. Biomaterials, 33, 5230-5246.
Hubschman, et al. (2010). 'The Microhand': a new concept of micro-forceps for ocular robotic surgery. Eye, 24, 364-367.
Aimi, M. F., Rao, M. P., Macdonald, N. C., Zuruzi, A. S., & Bothman, D. P. (n.d.). High-aspect-ratio bulk micromachining of titanium. Nature Materials, 3, 103-105. Retrieved from www.nature.comfnaturematerials.
EFAB Technology for Medical Devices: An Introduction Pamphlet. A Wafer-Based, 3-D Metal Micro-Manufacturing Technology for Ultraminiaturized Medical Devices Pamphlet.
Heriban, D., Gauthier, M., Regnier, S., Chaillet, N., Lutz, P. Automatic pick-and-place of 40 microns objects using a robotic platform. H. Van Brussel, E. Briksmeier, H. Spaan, T. Burke. 9t International Conference of the European Society for Pre-cision Engineering and Nanotechnology, EUSPEN'09., Jun 2009, San Sebastian, Spain. II, pp. 515-518, 2009. <hal-00404444>.
Research: Micro-Scale Surgical Tools_LIBNA.
Lieberman, D. M., M.D. ( Dec. 1976). Suturing Forceps for Microsurgery. American Journal of Ophthalmology, 82(6), 939-940.
Aoki, I, Takahashi, T., Mihara, S., Yamagata, Y., Higuchi, T., Trial Production of Medical Micro-Tool by Metal Deformation Processes Using Moulds, 344-349.
Dargahi, J., Parameswaran, M., & Payandeh, S. (n.d.). (Oct. 1998). A Micromachined Pizoelectric Tactile Sensor for use in Endoscopic Graspers. Intl. Conference on Intelligent Robots and Systems, 1503-1508.
Bustillo, J. L., M.D. (1975). Corneal Forceps. American Journal of Ophthalmology, 80(1), 152-153.
Gruber, A.E., et al. "Miniaturisierte Instrumente aus Nickel-Titan Legierungen fur die minimal Invasive Therapie [Miniaturized Instruments made from Nickel-Titanium Alloys for Minimally Invasive Therapy]" Karsruhe Research vol. 32 (2000): 70-76 Published 2000.
Semeraro, Francesco, et al. "Current Trends about Inner Limiting Membrane Peeling in Surgery for Epiretinal Membranes." Journal of Ophthalmology. vol. 2015 (2015), 13 pages.

* cited by examiner

US 10,973,682 B2

SURGICAL INSTRUMENT WITH ADHESION OPTIMIZED EDGE CONDITION

CROSS-REFERENCE TO RELATED APPLICATIONS

This application claims the benefit of U.S. Provisional Application No. 61/943,805, filed Feb. 24, 2014, which is incorporated herein by reference in its entirety.

TECHNICAL FIELD

The present disclosure generally relates to surgical instruments, and in particular to a forceps instrument for use in vitreoretinal surgeries having an adhesion-optimized edge condition to enhance the grasping and peeling of retinal membrane layers during a vitreoretinal procedure.

BACKGROUND

Vitreoretinal surgical procedures have been developed for restoring, preserving, and enhancing vision in patients suffering from a variety of injuries and/or age-related degenerative conditions. For example, vitreoretinal procedures, including vitrectomy procedures are used to repair damage to a patient's eye due to conditions such as macular degeneration, diabetic retinopathy, diabetic vitreous hemorrhage, detached retinas, as well as to repair complications from cataract surgeries and for removal and repair of damage due to foreign bodies within the patient's eye. Atraumatic peeling of internal limiting membranes ("ILM") within the patient's eye increases the chance of a successful vitreoretinal surgical procedure. These membrane peeling or membranectomy procedures generally remove portions of a surface or upper layer ILM covering the retina to remove damaged tissue and inhibit the growth of scar tissue across the macula of the patient's eye, and to reduce traction of the ILM to the underlying retina.

Typically, to perform a peeling procedure, the surgeon will use an extremely fine forceps, under high magnification, to try to grasp and gently peel away the ILM layer from the retina. Diamond dusted or other treated probes or instruments are used to scrape or pull the retinal tissue or an ILM layer into a condition where it can be grasped by the forceps for grasping and peeling of the ILM layer. Such an operation, however, is extremely delicate and requires a significant degree of precision as there is a danger of pressing and/or pinching too deeply into the ILM and underlying retinal tissue during such a peeling operation. This can result in possible infection, bleeding, retinal detachment, and damage of the underlying retina layer that can facilitate cataract progression. Typically, recurrence of epiretinal membranes forming across the macula generally occurs in approximately ten percent of patients following an initial vitreoretinal surgery involving such membrane peeling procedures.

SUMMARY

Briefly described, the present disclosure generally is directed to a surgical instrument with an adhesion optimized edge condition. According to one aspect, the disclosure describes a forceps including a body, pincers extending from a first end of the body, a grasping edge formed at distal end of at least one of the pincers, and a textured surface formed along at least a portion of the grasping edge. The pincers may be movable between an open configuration and a closed configuration. The textured surface may be configured to generate a capillary action with a contacted membrane as the pincers are moved into the closed configuration.

Another aspect of the disclosure encompasses a vitreoretinal forceps that includes a pair of spaced resilient pincers movable between an open configuration and a closed configuration, a textured surface formed along a distal end of each pincer comprising a plurality of cavities disposed at spaced intervals. The textured surface is configured to generate adhesion with a membrane adjacent to the pincers. The adhesion being formed by the membrane filling the plurality of cavities.

The various aspects may include one or more of the following features. The capillary action may be generated by the textured surface that substantially matches the adhesion of the membrane. The surface topography of the textured surface may be substantially non-uniform. A distal end of at least one of the pincers includes a rounded grasping edge. The rounded grasping edge may include a radius within the range of approximately 500 nm to approximately 30,000 nm. A distal tip of at least one of the pincers may include a chamfered tip with an angle of between about 25° and 45°. The textured surface may include an array of apertures and a plurality of peaks disposed between the apertures.

The various aspects may also include one or more of the following features. The textured surface may include a series of irregularly formed projections with the cavities defined therebetween. The cavities defined between the projections may be substantially non-uniform. The plurality of cavities may include an array of apertures, and wherein the textured surface further comprises a plurality of peaks formed between the apertures.

Various features, objects and advantages of the present disclosure will become apparent to those skilled in the art upon a review of the following detailed description, when taken in conjunction with the accompanying drawings.

Those skilled in the art will appreciate and understand that, according to common practice, the various features of the drawings discussed below are not necessarily drawn to scale, and that the dimensions of various features and elements of the drawings may be expanded or reduced to more clearly illustrate the example implementations of the present disclosure described herein.

DETAILED DESCRIPTION

The present disclosure describes various example implementations of surgical instruments configured to remove an internal limiting membrane ("ILM"). Particularly, the disclosure describes example vitreoretinal forceps for use in vitreoretinal surgical procedures. In particular, the disclosure describes vitreoretinal forceps adapted for use in vitrectomy or membrane peeling procedures in which the ILM, or other membranes, are engaged and peeled away from the retina. The vitreoretinal forceps are optimized such that an amount of force applied to the ILM by the forceps and/or a depth the forceps are pressed into the ILM is substantially minimized while, at the same time, is sufficiently engaging the ILM for removal from the retina. Consequently, the vitreoretinal forceps are operable to remove the ILM while reducing the potential for damage or injury to the underlying retinal tissue.

Figure 1:
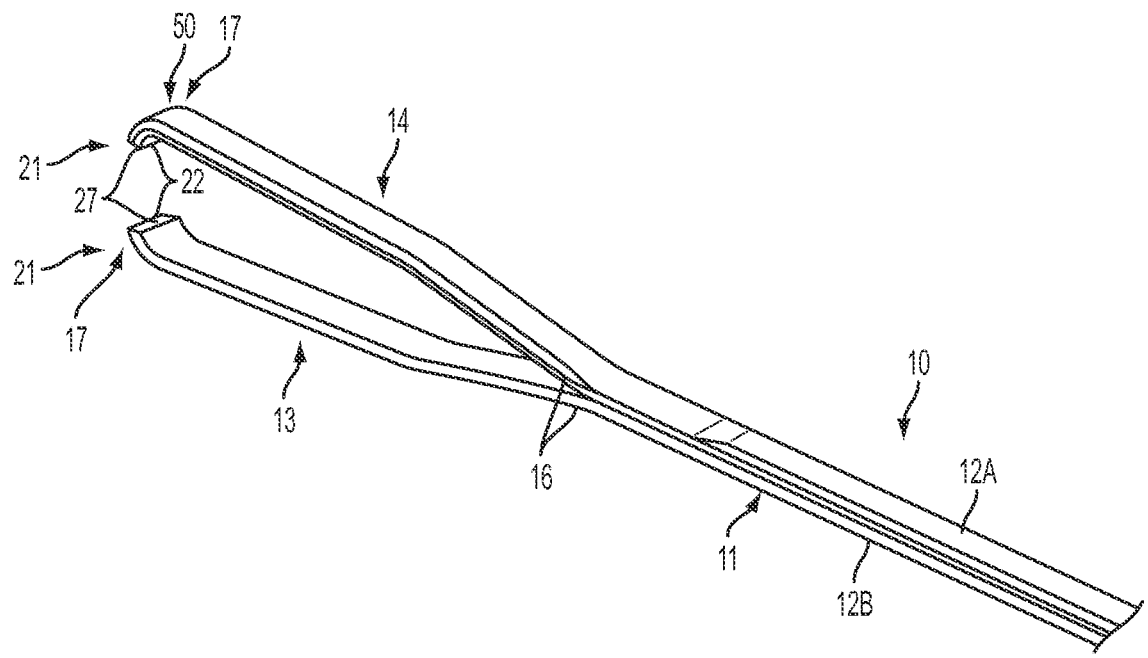
FIG. 1 is a perspective illustration of an example implementation of a forceps with an adhesion-optimized edge condition.
Figure 2:
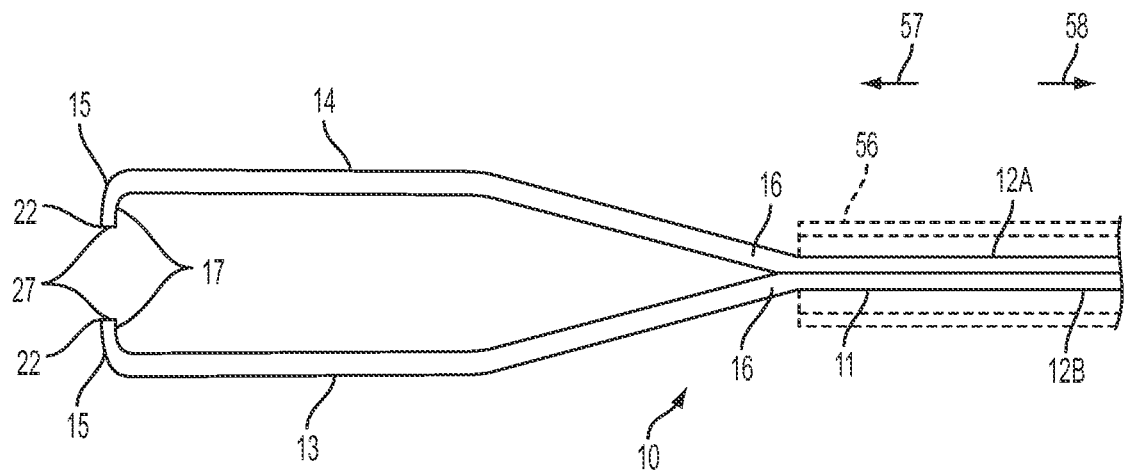
FIG. 2 is a top view of the example forceps shown in FIG. 1.
Figure 3:
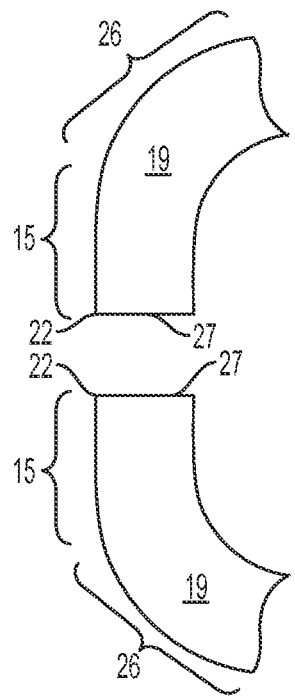
FIG. 3 is a detail view of distal ends of the pincers shown in FIG. 2.

Referring to FIGS. 1 through 3, the forceps 10 may include an elongated body 11. In some instances, the elongate body 11 may be formed from a pair of body sections 12A and 12B. The body sections 12A, 12B may be coupled together to form a unitary body structure. In other implementations, the elongated body 11 may be a unitary body. The elongated body 11 may be formed from any of a variety of materials. Particularly, the elongated body 11 may be formed from a medical grade material. For example, the elongated body 11 may be formed from a metal, such as titanium or stainless steel, nickel-titanium alloys or "Nitinol," or other similar alloy materials. Additionally, the elongated body 11 may be formed from a polymer, such as a medical grade plastic; synthetics materials (e.g., synthetic fibers or synthetic diamond); or composite materials. Also, the forceps 10 may be an instrument that is disposable after a single use. Alternately, the forceps 10 may be sterilizable and, thus, reusable.

Referring to FIGS. 2 and 3, the forceps 10 also includes a pair of pincers 13 and 14. The pincers 13, 14 include distal ends 17 that have a curved portion defining a hooked or C-shaped configuration. The curved nature of the distal ends 17 of the pincers 13, 14 permits the engaging surfaces 27 to be offset inwardly from the remainder of the pincers 13, 14. Further, with the distal ends 17 having a curved portion, the engaging surfaces 27 may be aligned with each other so as to substantially engage when the pincers 13, 14 are moved into the closed configuration.

Grasping surfaces 27 are defined at the distal end 17 of the pincers 13, 14. The grasping surfaces 27 are adapted to engage the ILM or other membranes. Also, grasping edges 22 may also be important in engaging and grasping the ILM or other membranes. The grasping edges 22 are a portion of an exterior surface of the pincers 13, 14 disposed between the grasping surfaces 27 and end surface 15. The pincers 13, 14 also include outer surfaces 26 that extend from end surfaces 15 along curvatures 19 of the pincers 13, 14. One or more of the grasping surfaces 27, the grasping edges 22, and the outer surfaces 26 may be enhanced to facilitate and/or optimize gripping and adhesion of the ILM or other membranes thereto.

The grasping edges 22 may be radiused or include a portion that is radiused. In some instances, a curvature of at least a portion of the grasping edges 22 may have a radius of 50 nm to 30,000 nm. However, in other instances, the radius may be larger or smaller than the indicated range. Additionally, in some instances, the exterior surface 15 may also be enhanced to promote adhesion with the ILM or other membranes.

The configuration of the grasping edge 22 provides for improved grasping of membranes, such as the ILM. For example, a radius of the grasping edge 22 (or a portion thereof) within the range identified above provides for enhanced grasping of the membrane. In some instances, the enhanced grasping reduces a force that must be applied to the membrane via the forceps in order to successfully grasp and remove the membrane. Consequently, risks associated with engaging, grasping, and removing membranes may be reduced. Further, as explained below, the grasping edges 22 may also include a textured surface. The textured surface further enhances adhesion of a membrane, thereby further reducing forces required to engage the membrane with the forceps. Again, the reduced forces further improve performance of the forceps and further reduces potential risks, e.g., harm to underlying tissues, associated with grasping and removal of membranes.

Figure 4:
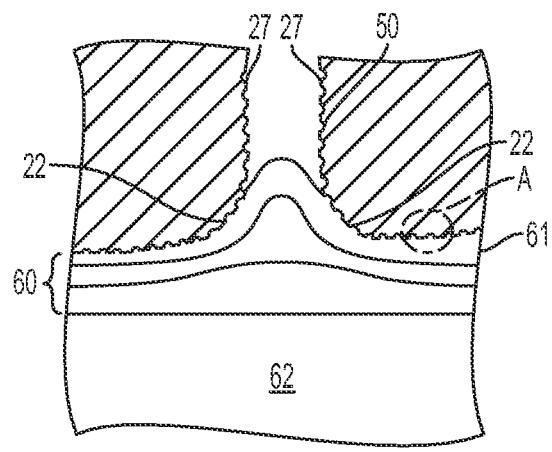
FIG. 4 is a partial cross-sectional view of example pincers engaging an ILM in which the engaging edges and engaging surface include a textured surface.

FIG. 4 shows a detail view of the distal ends 17 of the pincers 13, 14. Particularly, FIG. 4 shows the grasping surfaces 27 and the grasping edges 22 engaged with ILM 60. In the illustrated example, the grasping surfaces 27 and the grasping edges 22 include a textured surface 50.

The enhanced surface may be textured or otherwise formed with a roughened or patterned surface. The grasping surfaces 27 and, in some instances, both the grasping surfaces 27 and the grasping edges 22 are adapted to induce large adhesion forces on membranes engaged therewith. The textured surface 50 provides the grasping surfaces 27 and/or the grasping edges 22 with a surface condition that is optimized for engaging and grasping the ILM 60 or other membranes, for example, during a peeling operation. In still other implementations, one or more of the exterior surfaces 15, the outer surfaces 26, or one or more portions of these surfaces may also include a textured surface, such as textured surface 50, to enhance adhesion between the surface and a membrane.

Figure 5:
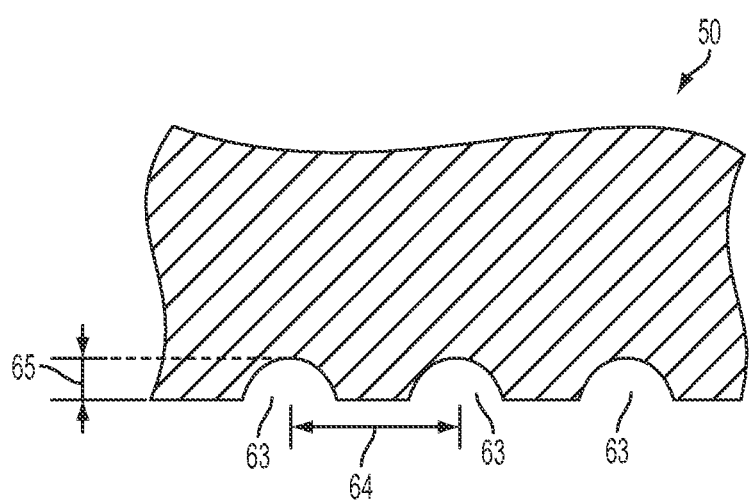
FIG. 5 is a detail view of a portion of the textured surface shown in FIG. 4.

FIG. 5 is a detail view of the textured surface 50 shown at location A in FIG. 4. In the example shown in FIG. 5, the texture surface 50 includes a plurality of recesses or apertures (collectively referred to hereinafter as recesses 63). The plurality of recesses 63 may be substantially uniformly distributed over the intended surfaces, for example, one or more of the grasping surfaces 27, grasping edges 22, and exterior surfaces 15. In some implementations, two or more of the recesses 63 may have a spacing 64 of approximately 100 µm and a depth 65 of approximately 6 µm. In other instances, though, the spacing 64 may be greater or less than 100 µm. Further, the depth 65 of recesses 63 may be greater or less than 6 µm. For example, in some instances, the space 64 and depth 65 of the plurality of recesses 63 may be selected based on a particular type of membrane to be engaged, the sensitivity of the membrane, or based on other considerations.

Figure 6:
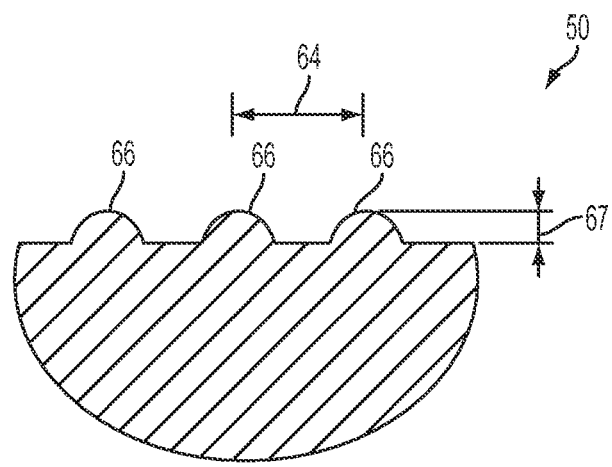
FIGS. 6-9 are detail views of other example textured surfaces.

The textured surface 50 may have other surface features. For example, FIG. 6 shows a detail cross-sectional view in which the textured surface 50 has a plurality of raised protrusions 66. In some instances, two or more of the protrusions 66 may be separated with a spacing 64 of approximately 100 µm. Further one or more of the protrusions 66 may have a height 67 of approximately 6 μm. In other instances, though, the spacing 64 may be greater or less than 100 μm. Further, the height 67 of protrusions 66 may be greater or less than 6 μm. For reasons similar to those explained above, the spacing 64 and height 67 of the protrusions 66 may be selected based on characteristics of the membrane to be grasped or other consideration associated with the membrane, such as location, proximity to other sensitive tissues, or other aspects related to the membrane.

Figure 7:
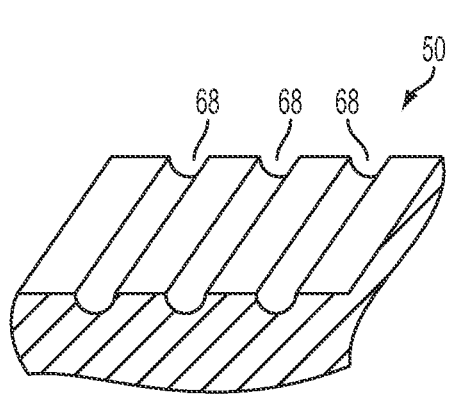

While FIGS. 5 and 6 show example features formed on and/or in the textured surface 50, the scope is not so limited. For example, in some instances, the textured surface 50 may include a plurality of grooves. FIG. 7 shows a portion of textured surface 50 in which a plurality of grooves 68 are formed. In some instances, two or more of the grooves 68 may be separated by 100 μm. Also, one or more of the grooves 68 may have a depth of 6 μm. However, as explained above, the spacing and depth of the grooves may vary.

Figure 8:
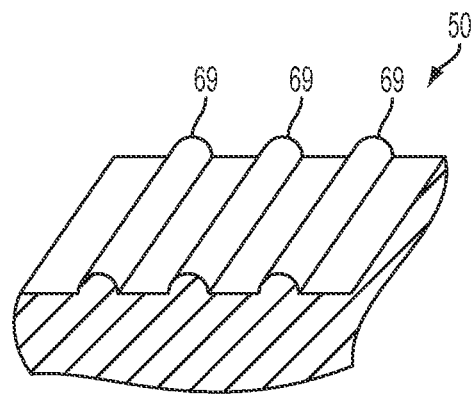
Figure 9:
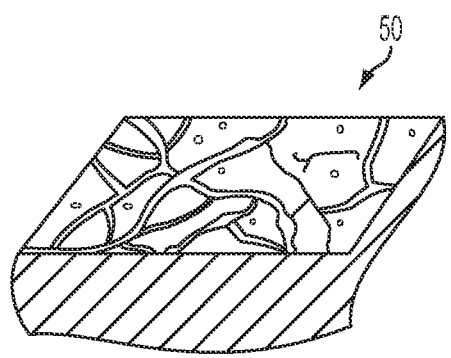

FIG. 8 shows an example textured surface 50 with a plurality of ridges 69. The ridges 69 may extend alone one or more portions of the surface, such as one or more of the grasping surfaces 27 or grasping edges 22. Spacing and heights of some of the ridges 69 may be similar to the spacing and heights described above, such as the spacing 64 and height 67. In some implementations, the textured surface 50 may have a random texture. For example, as shown in FIG. 9, the textured surface 50 may include a random distribution of surface features. For example, the textured surface 50 may include a random network of ridges, grooves, recesses, protrusions, or any combination thereof. Similar to the example textured surfaces described above, the textured surface 50 shown in FIG. 9 configured based on characteristics of the membrane to be grasped.

In still other implementations, the textured surface 50 may include two or more different textures described herein in a substantially uniform arrangement. In other implementations, the textured surface 50 may include two or more of the textures described herein in a substantially random arrangement. Further, the textured surface 50 may include substantially all of a single type of texture in which the dimensions and/or spacing of the features vary along the textured surface 50. In still other implementations, the texture surface 50 may include a plurality of the textures described herein in which the sizes and/or spacing of the textures vary along the textured surface 50. For example, the selection and/or arrangement of the textures may be selected so that the adhesion forces generated by the textured surface 50 is optimized for a type of membrane for which grasping is desired.

Further, the textured surface 50 may have a root mean squared (RMS) surface roughness of 1 to 10 microns (i.e., $1 \times 10^{-6}$ m to $10 \times 10^{-6}$ m). However, in other instances, the RMS surface roughness may be greater or less than 1 to 10 microns. The surface roughness of the textured surface 50 may vary based on characteristics of the membrane, such as one or more of the considerations described above.

The textured surface 50 may be formed using a variety of techniques. For example, the textured surfaces 50 may be formed by etching, electro-polishing, laser texturing, or other roughening or texturing techniques. As a result, in some implementations, the grasping edges 22, grasping surfaces 27, exterior surfaces 15, outer surfaces 26 or any combination thereof may be provided with a surface roughness that is operable to induce a capillary effect, fostering adhesion between a membrane, such as the upper layer 61 of the ILM 60, and the grasping edges 22, grasping surfaces 27, exterior surfaces 15, or outer surfaces 26 of the pincers 13, 14, as illustrated in FIG. 4. Thus, an optimized gripping or adhesive edge condition is created that enables enhanced gripping and/or adhesion between the forceps 10 and the ILM 60 with a minimal engaging force being applied to the ILM 60, as well as the underlying retina 62. The enhanced gripping provides for improved peeling of the membrane while substantially reducing the risk of damage to an underlying tissue.

As shown, for example, in FIGS. 1, 2, 10, 15, 17, and 18, the pincers 13 and 14 of the forceps 10 generally diverge or spread outwardly from their proximal ends 16 toward their distal ends 17 defining an open configuration. The pincers 13, 14 may be biased in the open configuration. For example, bias of the pincers 13, 14 into the open configuration may be provided by a natural or inherent resilience of a material from which the pincers 13, 14 and/or the elongated body 11 is formed.

The pincers 13, 14 are moveable into a closed configuration in which the distal ends 17 of the pincers 13, 14 are brought towards each other. In some instances, the distal ends 17 come into contact in the closed configuration. For example, in some implementations, the grasping surfaces 27 and/or the grasping edges 22 come into contact when the pincers 13, 14 are in the closed configuration. In other instances, the distal ends 17 of the pincers 13, 14 come into a close relationship such that the grasping surfaces 27 and/or the grasping edges 22 are directly adjacent to each other without contacting in the closed configuration, as shown, for example, in FIG. 3. In the closed configuration, the grasping surfaces 27 may be utilized for engaging and/or grasping a flap or other portion of a top layer 61 of the ILM. As such, the forceps 10 may be utilized to peel of the ILM 60 away from the retina 62.

Figure 10:
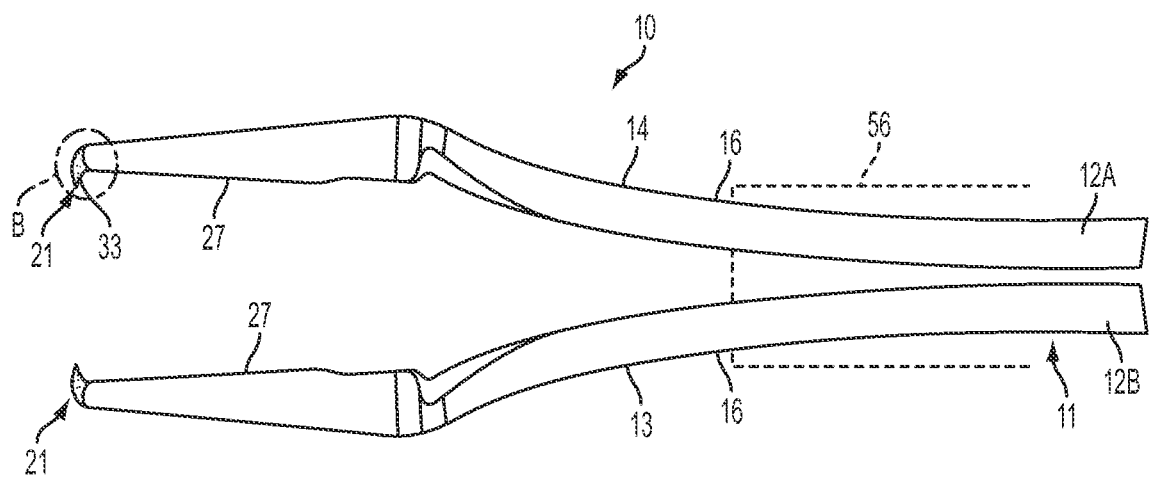
FIG. 10 is a top view of another example forceps.
Figure 11:
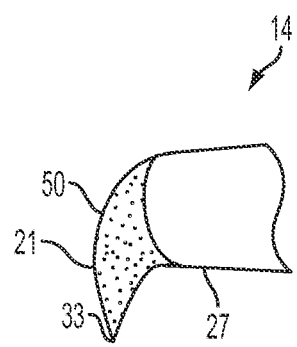
FIG. 11 is a detail view of a distal end of one of the pincers of the example forceps shown in FIG. 10.
Figure 12:
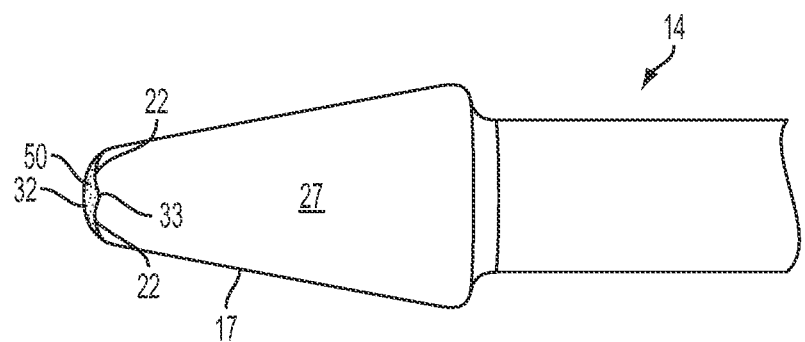
FIG. 12 is a side view of the distal end of the pincers of the example forceps shown in FIG. 10.

In other implementations, such as the examples shown in FIGS. 10 through 12, tips 21 of the pincers 13, 14 may taper in the distal direction. For example, in some instances, the tips 21 of the pincers 13, 14 may taper in two directions, as shown in FIGS. 10 and 12. In other instances, the taper of the tips 21 of the pincers 13, 14 may be in only a single direction. For example, the tips 21 of the pincers 13, 14 may taper distally in a first direction (e.g., as shown in FIG. 10) and not in a second direction (e.g., as shown in FIG. 12) or vice versa.

Figure 13:
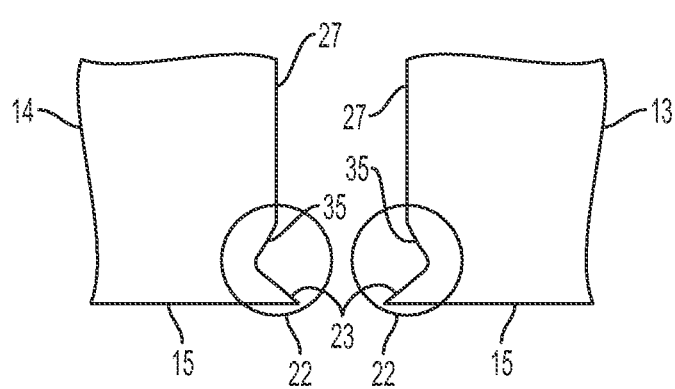
FIGS. 13-14 are detail views of the distal ends of the pincers of other example forceps.
Figure 14:
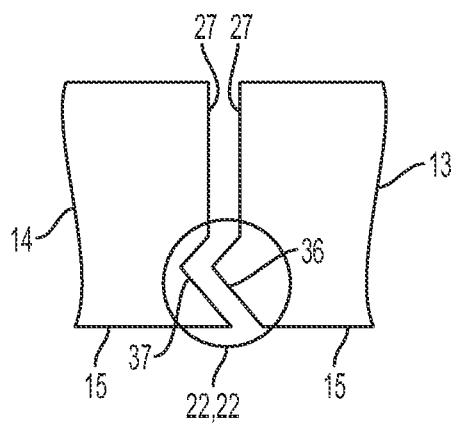
Figure 15:
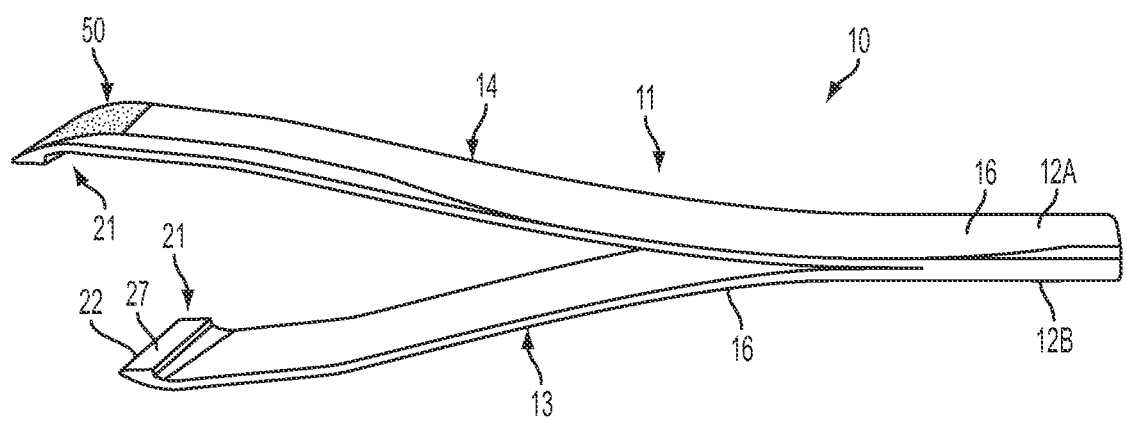
FIG. 15 a perspective view of another example forceps.

FIG. 13 shows a detail view of distal ends of example pincers 13, 14. The pincers 13, 14 include grasping edges 22 that include inwardly protruding tips 23. The grasping edge 22 of the pincers 13, 14 may also include recesses 35. Thus, in some implementations, the grasping edges 22 of the pincers 13, 14 may be symmetrical. In other implementations, the grasping edges 22 of the pincers 13, 14 may be asymmetrical. FIG. 14 shows grasping edges 22 of pincers 13, 14 that are asymmetrical. For example, the grasping edge 22 of pincer 13 may include a protrusion 36 that is received within a recess 37 of the grasping edge 22 of pincer 14.

Similar to the examples described above, the pincers 13, 14 shown in FIGS. 13 and 14 may also include a textured surface, such as one or more of the textured surfaces 50 described above, on one or more of the grasping edges 22, the end surfaces 15, or outer surfaces 26.

Referring again to FIGS. 10-12, the distal ends of the pincers 13, 14 may also include a rounded distal surface 32. FIG. 11 shows a detail of location B in FIG. 10 that shows the rounded distal surface 32. The rounded distal surface 32 may have a radius of curvature radius so as to define a shape corresponding to a shape of the retina. Further, the grasping edges 22 may extend continuously along the curved tip 21 of the pincers, as shown in FIG. 12. In the examples shown in FIGS. 10-12, the curved tips 21 define a reduced area for grasping a membrane, such as the ILM. In some implementations, one or more of the rounded distal surfaces 32, the grasping edges 22, or the grasping surfaces 27 may include a textured surface, such as one or more of the textured surfaces described above.

Figure 16:
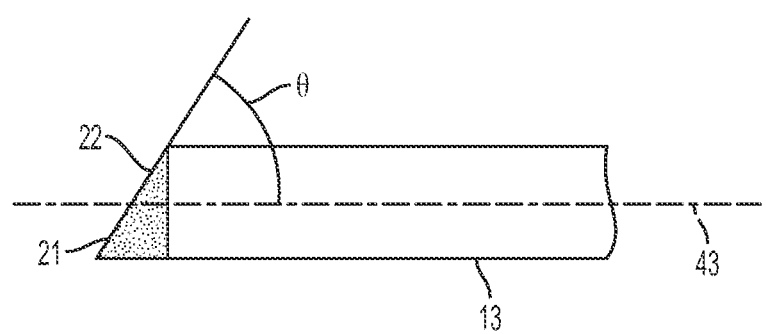
FIG. 16 shows a side view of a portion of the pincers shown in FIG. 15.

FIGS. 15-18 illustrate another example forceps 10. As shown in FIG. 16, the tips 21 may be chamfered so as to define an angle θ between grasping edges 22 and longitudinal axis 43. In some instances, the angle θ may be approximately 25° to 45°. However, the angle θ may be any desired angle. The grasping surfaces 27 of the pincers 13, 14 may be substantially flat.

Figure 17:
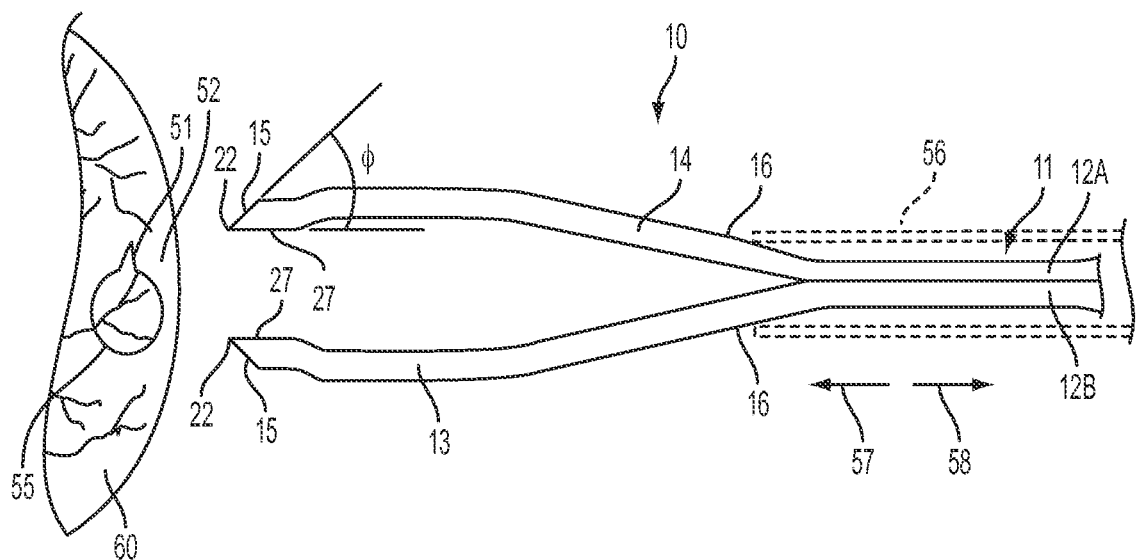
FIG. 17 is a top view of the example forceps shown in FIG. 15 in an open configuration.

In addition, as illustrated in FIG. 17, the exterior surfaces 15 of the pincers 13, 14 may also be formed at an angle φ. In some instances, the angle φ of the exterior surfaces 15 relative to the grasping surfaces 27 may be approximately 25° to 45°. However, the angle φ of the outer side surfaces 44 may be disposed at an angle greater or smaller than this range. As explained above, one or more of the grasping edges 22, grasping surfaces 27, or exterior surfaces 15 may include a texture, such as one or more of the textured surfaces 50 described above.

A shape of the grasping edges 22, the grasping surfaces 27, the exterior surfaces 15, and/or the outer surfaces 26 may be selected to further enhance the grasping performance of the pincers 13, 14. For example, the geometries of one or more of these features may be selected to enhance grasping performance. Further, the geometry of these features as well as the textured surface(s) 50 applied to one or more of the features may also be selected to enhance (e.g., optimize) capillary action, thereby enhancing (e.g., maximizing) adhesion between the forceps 10 and a particular membrane. Characteristics of the membrane, such as elasticity and thickness of the membrane, may also be considered in selecting a textured surface 50.

Enhanced attraction between the forceps 10 and a membrane, such as the ILM, results in an enhanced or increased capillary force to cause a membrane (e.g., the top layer of the ILM) to flow around or about the surface features of the textured surface 50 and into the gap formed between the grasping surfaces 27. This enhanced capillary effect in turn increases and/or enhances the adhesion force between the forceps 10 and the ILM 60. At the same time, the enhanced capillary effect enables ILM peeling to be performed with a reduction in pressure applied to the ILM and underlying tissues as well as minimization of scraping forces being applied to the ILM and underlying retina by the forceps 10 when gripping and peeling of the ILM. Consequently, the risk of injury to the underlying tissues, such as the retina, is substantially reduced during a peeling operation.

Figure 18:
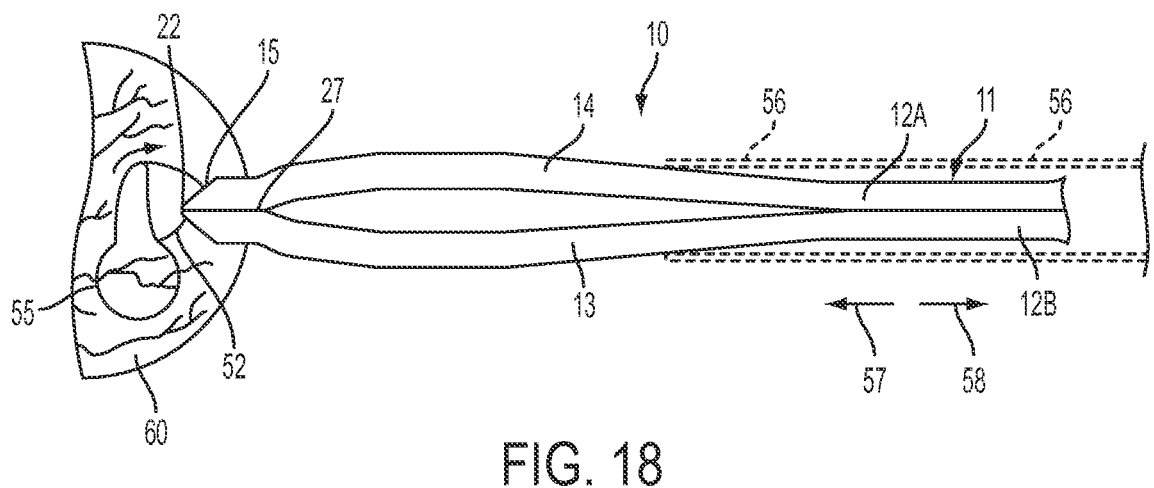
FIG. 18 is a top view of the example forceps shown in FIG. 15 in a closed configuration.

Referring to FIG. 18, in some implementations, after an incision 51 is made in the upper layer 61 of the ILM 60, the forceps 10 may be used to scrape and engage a flap 52 formed by the incision 51 or other portion of the ILM 60 for peeling. As the grasping edges 22 are moved into engagement with the ILM 60 at an incision site 55, an outer sleeve 56 of the forceps 10 may be moved relative to the forceps 10 in the direction of arrow 57. FIGS. 2, 17, and 18 illustrate operation of the sleeve 56. The sleeve 56 engages the pincers 13, 14 and urges the pincers 13, 14 into their closed configuration. Consequently, the pincers 13, 14 close and engage the ILM 60. Referring to FIG. 18, as the pincers 13, 14 are urged toward their closed configuration, the grasping edges 22 alone or in combination with one or more of the grasping surfaces 27, exterior surfaces 15, or outer surfaces 26 of the pincers 13, 14 engage and scrape or urge a portion of the ILM 60 inwardly. The ILM 60 is pulled and pinched between the grasping edges 22. Thereafter, the forceps 10 can be used to pull or peel the ILM 60 away from the underlying retina 62. The underlying retina 62 is unaffected and remains substantially untouched, thereby minimizing the damage thereto. When peeling has been completed, the sleeve 56 may be moved in the direction of arrow 58. As a result, the sleeve 56 disengages the pincer 13, 14 and the inherent bias of the pincers 13, 14 into the open configuration causes the pincers 13, 14 to return to the open configuration, releasing the ILM.

The foregoing description generally illustrates and describes various example implementations of the present disclosure. It will, however, be understood by those skilled in the art that various changes and modifications can be made to the above-discussed construction without departing from the spirit and scope of the disclosure. It is also intended that all matter contained in the above description or shown in the accompanying drawings shall be interpreted as being illustrative, and not to be taken in a limiting sense. Furthermore the scope of the present disclosure shall be construed to cover various modifications, combinations, additions, alterations, etc., to the above-described examples, which shall be considered to be within the scope of the present disclosure. Accordingly, various features and characteristics of the present disclosure as discussed herein may be selectively interchanged and applied to other illustrated and non-illustrated implementations of the disclosure, and numerous variations, modifications, and additions further can be made thereto without departing from the spirit and scope of the present disclosure as set forth in the appended claims.

What is claimed is:

1. A forceps comprising:
a body;
a first pincer and a second pincer extending from a first end of the body, the first pincer and the second pincer movable between an open configuration and a closed configuration, each of the first pincer and the second pincer comprising:
a longitudinally extending portion;
a hook-shaped curved portion formed at a distal end of the longitudinally extending portion, the hook-shaped curved portion curved inwardly and terminating with a grasping surface, the grasping surface of the first pincer and the grasping surface of the second pincer facing each other;
an end surface formed along a distal side of the hook-shaped curved portion, the end surface formed adjacent to the grasping surface;
a grasping edge extending between the grasping surface and the end surface; and
a textured surface formed along at least a portion of the end surface, the textured surface configured to generate a capillary action with a contacted membrane as the pincers are moved into the closed configuration,
wherein the grasping edge of each of the first pincer and the second pincer defines a rounded surface such that the end surface, the grasping edge and the grasping surface define a continuous surface.

2. The forceps of claim 1, wherein the textured surface comprises a plurality of protrusions and valleys formed therebetween defining a surface topography, and wherein the capillary action is operable to cause the membrane to be accepted into the valleys.

3. The forceps of claim 2, wherein the surface topography of the textured surface of each of the first pincer and the second pincer is non-uniform.

4. The forceps of claim 1, wherein the rounded grasping edge of each of the first pincer and the second pincer comprises a radius within the range of approximately 500 nm to approximately 30,000 nm.

5. The forceps of claim 1, wherein a distal tip of at least one of the first pincer and the second pincer comprises a chamfered tip with an angle of between about 25° and 45°.

6. The forceps of claim 1, wherein the textured surface of each of the first pincer and the second pincer comprises an array of apertures and a plurality of peaks disposed between the apertures.

7. The forceps of claim 1, wherein the textured surface comprises a plurality of raised protrusions.

8. The forceps of claim 7, wherein a height of the plurality of raised protrusions is approximately 6 μm.

9. The forceps of claim 7, wherein a height of the plurality of raised protrusions is less than 6 μm.

10. The forceps of claim 7, wherein a separation spacing between two or more of the raised protrusions is less than 100 μm.

11. The forceps of claim 1, wherein a distal tip of at least one of the first pincer and the second pincer comprises a chamfered tip with an angle of between about 25° and 45°.

12. The forceps of claim 1, wherein the textured surface of each of the first pincer and the second pincer comprises an array of apertures and a plurality of peaks disposed between the apertures.

13. A vitreoretinal forceps comprising:
   a pair of spaced resilient pincers movable between an open configuration and a closed configuration, each of the pair of pincers comprising:
      a longitudinally extending portion;
      a hook-shaped curved portion formed at a distal end of the longitudinally extending portion, the hook-shaped curved portion curved inwardly and terminating with a grasping surface, the hook-shaped curved portion comprising:
         an inwardly extending portion; and
         a curved portion disposed between the inwardly extending portion and the longitudinally extending portion, the grasping surface of each of the pincers facing each other;
      an end surface formed along the inwardly extending portion, the end surface formed adjacent to the grasping surface;
      a rounded grasping edge extending between the grasping surface and the end surface; and
   a textured surface formed along the end surface of each pincer comprising a plurality of raised protrusions disposed at spaced intervals, the textured surface configured to generate a capillary action with a contacted membrane adjacent to the pincers as the pincers are moved into the closed configuration, and
   wherein the grasping edge of each of the first pincer and the second pincer defines a rounded surface such that the end surface, the grasping edge and the grasping surface define a continuous surface;
   wherein the textured surface is not formed along the longitudinally extending portion of the pincers.

14. The vitreoretinal forceps of claim 13, wherein the textured surface comprises a series of cavities.

15. The vitreoretinal forceps of claim 14, wherein the cavities defined between the projections are non-uniform.

16. A forceps comprising:
   a body;
   a first pincer and a second pincer extending from a first end of the body, the first pincer and the second pincer movable between an open configuration and a closed configuration, each of the first pincer and the second pincer comprising:
      a longitudinally extending portion;
      a hook-shaped curved portion formed at a distal end of the longitudinally extending portion, the hook-shaped curved portion curved inwardly and terminating with a grasping surface, the grasping surface of the first pincer and the grasping surface of the second pincer facing each other, the hook-shaped curved portion comprising:
         an inwardly extending portion; and
         a curved portion disposed between the inwardly extending portion and the longitudinally extending portion;
      an end surface formed along inwardly extending portion and disposed adjacent to the grasping surface;
      a grasping edge extending between the grasping surface and the end surface; and
      a textured surface formed along at least a portion of the end surface and not extending along the longitudinally extending portion, the textured surface configured to generate a capillary action with a contacted membrane as the pincers are moved into the closed configuration;
   wherein the grasping edge of each of the first pincer and the second pincer defines a rounded surface such that the end surface, the grasping edge and the grasping surface define a continuous surface.

17. The forceps of claim 16, wherein the textured surface comprises a plurality of protrusions and valleys formed therebetween defining a surface topography, and wherein the capillary action is operable to cause the membrane to be accepted into the valleys.

18. The forceps of claim 17, wherein the surface topography of the textured surface of each of the first pincer and the second pincer is non-uniform.

* * * * *